United States Patent [19]

Fiato et al.

[11] 4,273,936

[45] Jun. 16, 1981

[54] RHODIUM-CATALYZED OXIDATION PROCESS FOR PRODUCING CARBOXYLIC ACIDS

[75] Inventors: Rocco A. Fiato, Charleston, W. Va.; Roy L. Pruett, New Providence, N.J.

[73] Assignee: Union Carbide Corporation, New York, N.Y.

[21] Appl. No.: 159,859

[22] Filed: Jun. 16, 1980

Related U.S. Application Data

[63] Continuation-in-part of Ser. No. 79,884, Sep. 28, 1979, abandoned.

[51] Int. Cl.$^3$ .............. C07C 53/122; C07C 51/145; C07C 51/235
[52] U.S. Cl. ............................ 562/606; 562/512; 562/522; 562/531; 562/544; 260/546; 568/454
[58] Field of Search ............ 562/512, 522, 531, 544; 562/606; 260/546

[56] References Cited

U.S. PATENT DOCUMENTS

| | | | |
|---|---|---|---|
| 2,815,355 | 12/1957 | Hill | 562/531 |
| 3,415,871 | 12/1968 | Olivier | 562/522 |
| 3,637,833 | 1/1972 | Fenton | 562/522 |
| 3,954,877 | 5/1976 | Gipson | 568/909 |
| 4,196,096 | 4/1980 | Dunes et al. | 252/414 |

FOREIGN PATENT DOCUMENTS

| | | | |
|---|---|---|---|
| 2604545 | 8/1977 | Fed. Rep. of Germany. | |
| 922694 | 4/1963 | United Kingdom | 562/544 |

*Primary Examiner*—Joseph E. Evans
*Attorney, Agent, or Firm*—Reynold J. Finnegan

[57] ABSTRACT

A one-step process is disclosed for forming a carboxylic acid and its anhydride directly from the corresponding olefin which comprises reacting the olefin with carbon monoxide, hydrogen and oxygen in the presence of a stable rhodium complex catalyst. The rhodium catalyst is stabilized by a pentavalent Group V ligand, such as a phosphine oxide. The reaction is preferably conducted in an inert organic solvent. In an alternate embodiment, a carboxylic acid may be obtained by oxidation of an aldehyde (produced, for example, by hydroformylation of the corresponding olefin) in the presence of a rhodium complex catalyst stabilized by a pentavalent Group V ligand. This reaction is also preferably conducted in an inert organic solvent.

24 Claims, No Drawings

RHODIUM-CATALYZED OXIDATION PROCESS FOR PRODUCING CARBOXYLIC ACIDS

This application is a continuation-in-part of U.S. application Ser. No. 079,884, filed Sept. 28, 1979 now abandoned.

BACKGROUND OF THE INVENTION

1. Field of the Invention

The present invention generally relates to a process for forming carboxylic acids; more particularly, to a rhodium-catalyzed one-step process for forming a carboxylic acid directly from the corresponding olefin and to a rhodium-catalyzed process for oxidizing an aldehyde to form the corresponding carboxylic acid.

2. Description of the Prior Art

Carboxylic acids have many uses in the chemical industry. For example, propionic acid is useful as a grain preservative and higher acids have been used in the manufacture of detergents.

Many different processes are known for preparing carboxylic acids, such as hydroformylation of an olefin followed by oxidation of the resulting aldehyde. The acid produced has a carbon number one higher than the olefin. For example, an olefin (e.g., ethylene) is hydroformylated by reaction with carbon monoxide and hydrogen to produce the corresponding aldehyde (propionaldehyde) which is then in turn oxidized to the corresponding acid (propionic acid). In some cases, after the hydroformylation reaction of the olefin with carbon monoxide and hydrogen, also known as an oxo process, the aldehyde is recovered and purified before oxidizing it to the acid.

Other related processes of the prior art do not require purification of the aldehyde. For example, West German Pat. No. 2,604,545 discloses a two-step method for preparing alkylcarboxylic acids by hydroformylating the corresponding olefin at high pressures of 100 to 600 bars and directly oxidizing the resulting aldehyde-containing reaction mixture, both steps being conducted in the presence of a rhodium carbonyl complex catalyst.

U.S. Pat. No. 3,980,670 discloses a process for simultaneously obtaining both methacrylic acid and butyrolactone by first hydroformylating allyl esters of lower fatty acids in the presence of both rhodium carbonyl complex catalysts and inert organic solvents, followed by directly oxidizing the resulting reaction mixture in the presence of lower fatty acids and recovering the products after separation of a residue including the rhodium catalyst.

U.S. Pat. No. 3,520,937 discloses a technique for processing cobalt- and aldehyde-containing oxo reaction mixtures with an oxidizing agent to provide a cobalt-free material. The amount of oxygen is disclosed to be insufficient to oxidize the product aldehyde.

Still other prior art processes provide for directly oxidizing or carboxylating an olefin to produce various products. For example, U.S. Pat. No. 3,384,669 discloses a process for converting an olefin to the corresponding aldehyde or ketone by oxidation with molecular oxygen in the presence of a catalyst which comprises an aqueous solution of varivalent noble metal ions and either nitrate or nitrite ions or a mixture thereof.

West German Pat. No. 2,744,207 discloses a method of oxidizing an olefin to, for example, a ketone by reacting the olefin, in the absence of an inert solvent to facilitate product recovery, in a reaction medium comprising an organic phosphine or phosphite in the presence of a rhodium complex catalyst and a stabilizing phosphine or phosphite ligand.

U.S. Pat. No. 3,818,060 discloses a Group VIII metal-catalyzed hydrocarboxylation process for forming carboxylic acids comprising reacting an olefin with carbon monoxide and water. The catalyst system comprises an iridium or rhodium-containing compound, a halide promoter and a stabilizer composed of an organic derivative of pentavalent phosphorus, arsenic, antimony, nitrogen or bismuth. The stabilizers are disclosed as preventing precipitation and solids deposition which would ordinarily adversely affect catalyst stability. See also U.S. Pat. Nos. 3,816,488, 3,816,489 and 3,944,604.

Blum et al., in *Tetrahedron Letters* No. 38, pp. 3665–3668 (1967) disclose the alpha-oxidation of alkylbenzenes by the rhodium complex catalyst chlorotris(triphenylphosphine) rhodium, $RhCl(PPh_3)_3$ (where "Ph"=phenyl). Specifically, the alkylbenzene ethylbenzene is oxidized by air to acetophenone in the presence of the catalyst.

Fusi et al., in *Journal of Organometallic Chemistry* 26 (1971) pp. 417–430, propose a mechanism for the oxidation of cyclohexene by transition metal complexes. Specific results are given for the oxidation of cyclohexene to cyclohexene oxide, cyclohexanone and cyclohexanol in the presence of various catalysts, including rhodium complexed with triphenyl phosphine.

Takao et al., in *Bulletin of the Chemical Society of Japan*, 43 (12) December, 1970, pp. 3898–3900, report on the oxidation of the olefin styrene with the rhodium complex chlorotris(triphenylphosphine) rhodium or rhodium chloride, and the effect of various solvents on the oxidation products. In a non-polar solvent such as toluene, the main products were both acetophenone and benzaldehyde. The oxidation of methylstyrenes with the same catalysts is also reported.

In a later publication by Takao et al., *Bulletin of the Chemical Society of Japan*, 45(5) May, 1972, pp. 1505–1507, the oxidation of cinnamaldehyde catalyzed by rhodium complexes in various solvents is reported. Two rhodium complexes, chlorocarbonylbis(triphenylphosphine) rhodium and chlorotris (triphenylphosphine) rhodium, were found to cause the catalytic oxidation of cinnamaldehyde in toluene to give benzaldehyde, glyoxal, benzene and styrene.

In *Bulletin of the Chemical Society of Japan*, 45(7) July, 1972, pp. 2003–2006, Takao et al. report on the oxidation, in a solvent, of vinyl esters catalyzed with chlorotris (triphenylphosphine) rhodium. The particular reaction products obtained are determined, in part, by the substitutent on the olefinic carbon atom. For example, vinyl acetate was oxidized in toluene to give acetone, propionaldehyde and methyl vinyl ether; while methyl ethyl ketone, butyraldehyde and ethyl vinyl ether were obtained from vinyl propionate.

Dudley et al., in *J.C.S. Dalton*, (1974) pp. 1926–1931, disclose the rhodium-promoted oxidation of α-olefins to methyl ketones in benzene. Two rhodium complexes, chlorotris(triphenylphosphine) rhodium and carbonylhydridotris (triphenylphosphine) rhodium, are shown to catalyze the reaction.

Mercer et al., in *Journal of the American Chemical Society* 97 (7) April, 1975, pp. 1967–1968, disclose that the rhodium complex $Rh_6(CO)_{16}$ catalyzes the oxidative cleavage of carbon-carbon bonds in ketones to carboxylic acids. A specific reaction reported involved suspending the rhodium in cyclohexanone as a solvent and pressurizing with oxygen, to produce adipic acid.

Various other prior art disclose methods of hydroformylation in which the presence of oxygen retards the reaction. For example, Polievka et al., in *Petrochemia* 1979, 19 (1-2), 5-12, disclose the low pressure hydroformylation of olefins (1-octene, di- and tri-isobutylene, allyl alcohol, styrene and dipentene) with a rhodium complex catalyst, $HRh(CO)(PPh_3)_3$ (where "Ph"=phenyl). The authors disclose that compounds such as oxygen, which are more reactive toward the catalyst than alkenes or CO, form stable complexes which retard the hydroformylation.

Matsui et al., in *Bulletin of the Japan Petroleum Institute*, 19, No. 1, May 1977, propose a mechanism to explain the observed deactivation of rhodium complex catalysts used in hydroformylation reactions. The specific catalysts reported on comprise rhodium, as $Rh_2Cl_2(CO)_4$, complexed with a triphenyl phosphite ligand. The authors concluded that catalyst deactivation was mainly due to the oxidation of triphenyl phosphite to triphenyl phosphate by the small amount of oxygen present in the synthesis gas.

The prior art also teaches the reactivation of deactivated rhodium complex catalysts with oxygen. For example, Japanese Pat. No. 51-23212 discloses a rhodium-catalyzed hydroformylation process and particularly a technique for reactivating the rhodium catalyst which becomes deactivated during the process by treating the deactivated rhodium catalyst in a separate step with oxygen and then recycling the reactivated catalyst back to the hydroformylation reaction.

Commonly-assigned, copending U.S. patent application Ser. No. 703,130 (published as Belgian Pat. No. 856,542) now U.S. Pat. No. 4,221,743 discloses a hydroformylation process in which a deactivated rhodium complex catalyst may be reactivated by bleeding small catalytic quantities of oxygen into the hydroformylation reaction system. The amount of oxygen employed is small (i.e., sufficient only to detoxify and reactivate the catalyst) and substantially all of the oxygen is consumed by the ligand in the catalyst to free the catalytic rhodium and thereby reactivate the catalyst.

Other prior art disclose hydroformylation processes where oxygen is present. For example, U.S. Pat. No. 3,920,754 discloses a hydroformylation process for forming formyl- and hydroxymethyl-substituted alkene derivatives by reacting the alkene with carbon monoxide and hydrogen in the presence of a free-radical initiator which preferably is molecular oxygen.

U.S. Pat. No. 3,954,877 discloses an olefin hydroformylation process which employs a complex of a Group VIII metal (e.g., rhodium) with a ligand comprising a pentavalent phosphorus, arsenic or antimony compound (e.g., phosphine oxides).

U.S. Pat. No. 3,555,098 discloses a Group VIII noble metal-catalyzed hydroformylation reaction wherein catalytic activity is maintained by treating all or a portion of a recycled reaction medium containing the catalyst with an alkaline aqueous solution to extract by-product carboxylic acids which otherwise deactivate the catalyst. The acids are believed to be formed by the slight oxidation of the product aldehyde due to oxygen contamination of the reactant gas streams.

For many years, all commercial hydroformylation reactions employed cobalt carbonyl catalysts which required relatively high pressures (often on the order of 100 atmospheres or higher) to maintain catalyst stability. U.S. Pat. No. 3,527,809, issued Sept. 8, 1970, to R. L. Pruett and J. A. Smith, discloses a significantly new hydroformylation process whereby alpha-olefins are hydroformylated with carbon monoxide and hydrogen to produce aldehydes in high yields at low temperatures and pressures, where the normal to iso- (or branched-chain) aldehyde isomer ratio of the product aldehydes is high. This process employs certain rhodium complex catalysts and operates under defined reaction conditions to accomplish the olefin hydroformylation. Since this new process operates at significantly lower pressures than required theretofore in the prior art, substantial advantages were realized including lower initial capital investment and lower operating costs. Further, the more desirable straight-chain aldehyde isomer could be produced in high yields.

The hydroformylation process set forth in the Pruett and Smith patent noted above includes the following essential reaction conditions:

(1) A rhodium complex catalyst which is a complex combination of rhodium with carbon monoxide and a triorganophosphorus ligand. The term "complex" means a coordination compound formed by the union of one or more electronically rich molecules or atoms capable of independent existence with one or more electronically poor molecules or atoms, each of which is also capable of independent existence. Triorganophosphorus ligands whose phosphorus atom has one available or unshared pair of electrons are capable of forming a coordinate bond with rhodium.

(2) An alpha-olefin feed of alpha-olefinic compounds characterized by a terminal ethylenic carbon-to-carbon bond such as a vinyl group, $CH_2=CH-$. They may be straight chain or branched chain and may contain groups or substituents which do not essentially interfere with the hydroformylation reaction, and they may also contain more than one ethylenic bond. Propylene is an example of a preferred alpha-olefin.

(3) A triorganophosphorus ligand such as a triarylphosphine. Desirably each organo moiety in the ligand does not exceed 18 carbon atoms. The triarylphosphines are the preferred ligands, an example of which is triphenylphosphine.

(4) A concentration of the triorganophosphorus ligand in the reaction mixture which is sufficient to provide at least two, and preferably at least 5, moles of free ligand per mole of rhodium metal, over and above the ligand complexed with or tied to the rhodium atom.

(5) A temperature of from about 50° to about 145° C., preferably from about 60° to about 125° C.

(6) A total hydrogen and carbon monoxide pressure which is less than 450 pounds per square inch absolute (psia), preferably less than 350 psia.

(7) A maximum partial pressure exerted by carbon monoxide no greater than about 75 percent based on the total pressure of carbon monoxide and hydrogen, preferably less than 50 percent of this total gas pressure.

In commercial hydroformylation-oxidation processes for producing carboxylic acids, the resulting aldehyde is usually recovered and then oxidized to the corresponding acid. Where the oxidation step is conducted without an aldehyde purification step and employing Group VIII metal catalysts, such as a rhodium-based catalyst, severe catalyst stability and activity problems are encountered when the oxidation is conducted in the presence of an inert aromatic or aliphatic solvent. Even without inert solvents, in the hydroformylation-oxidation route of olefin to acid, it has been necessary in the prior art to conduct the process in two stages (i.e., hydroformylation followed by a separate oxidation without aldehyde purification).

SUMMARY OF THE INVENTION

The present invention comprises a process for producing carboxylic acids and their anhydrides either directly from an olefin by reacting the olefin with carbon monoxide, hydrogen and oxygen in a single step using a stable rhodium complex catalyst or by oxidizing an aldehyde in the presence of a stable rhodium complex catalyst, wherein the stability and activity of the rhodium catalyst is maintained in both cases by employing in the catalyst a pentavalent Group V ligand. A catalyst system is thus provided which is stable under both hydroformylation and oxidation reaction conditions, even in an inert organic solvent. The process of the invention enables the acid and its anhydride to be produced directly from the corresponding olefin in a single operation with a single, stabilized catalyst. Alternatively, the hydroformylation and oxidation stages of such a process may, if desired, be separated by first separating and purifying the oxo aldehyde and then oxidizing it in accordance with the present invention. The rhodium complex catalyst is stable even when this oxidation is conducted in an inert organic solvent.

DESCRIPTION OF THE PREFERRED EMBODIMENTS

According to the present invention, a carboxylic acid having from 3 to about 21 carbon atoms (or higher) may be prepared in one of two ways. The first embodiment of the present invention, which for ease of reference only its referred to herein as a hydroformylation-oxidation process, is a one-step process comprising reacting an olefin, preferably in an inert organic solvent, with carbon monoxide, hydrogen and oxygen in the presence of a rhodium complex catalyst to produce the corresponding acid having one more carbon atom than the olefin. The second embodiment of the present invention comprises oxidizing an aldehyde, preferably in an inert organic solvent, in the presence of a rhodium complex catalyst to produce the corresponding acid.

In both cases, the rhodium complex catalyst includes a pentavalent Group V ligand which stabilizes the catalyst against deactivation. In the first embodiment, the precise mechanism by which an olefin is converted into a carboxylic acid is unknown. However, this embodiment does offer the advantage of producing the acid in a single process step as compared to those prior art processes which require the preparation of an aldehyde, optionally recovering and purifying the aldehyde, followed by oxidation thereof in a separate step to the corresponding acid.

In the process of the second embodiment of the invention, the aldehyde starting material may be prepared by any suitable means, such as by hydroformylation of the corresponding olefin.

The so-called hydroformylation-oxidation process of the invention is generally conducted by feeding make-up gas (which usually comprises olefin, hydrogen, carbon monoxide and oxygen) into a liquid reaction medium containing a catalytic quantity of rhodium complexed with a stabilizing pentavalent Group V ligand, at a temperature and pressure sufficient to directly produce the corresponding carboxylic acid. Preferably, the reaction is conducted in an inert organic solvent.

The olefin which may be reacted in the one-step hydroformylation-oxidation process of the invention may be any olefin having from 2 to about 20 carbon atoms and a single ethylenic carbon-to-carbon bond. The olefin may be straight-chain or branched-chain and may contain groups or substituents which do not essentially interfere with the course of the reaction. In addition, it is intended to include both alpha-olefins as well as internal olefins within the scope of the present invention. Typical alpha-olefins include, for example, ethylene, propylene, 1-butene, 1-pentene, 1-hexene, 1-heptene, 1-octene, 1-nonene, 1-decene, 1-undecene, 1-dodecene, and higher carbon analogs. The most preferred alpha-olefin is ethylene. Typical internal olefins include, for example, 2-butene, 2-pentene, 2- or 3-hexene, 3-decene, 4-decene, 2-undecene, 3-undecene, 4-undecene, 5-undecene, and higher carbon analogs.

The temperature of reaction is not critical and may generally be from about 75° to about 200° C. Above about 200° C., the catalyst may become deactivatd at reasonable operating pressures while below about 75° C., it may be difficult to achieve a desirable rate of reaction. The preferred reaction temperature is from about 95° to about 110° C.

The reaction may be conducted at a total gas pressure (of olefin, hydrogen, carbon monoxide and oxygen) of from about 100 to about 1000 pounds per square inch absolute (psia). The maximum pressure under which the reaction may be conducted is not particularly critical and, in reality, is limited primarily by economic considerations. With regard to the minimum pressure, below about 100 psia the rate of reaction may become low and in addition the rhodium complex catalyst may tend to become less stable. The preferred total gas pressure is from about 250 to about 350 psia.

As noted above, the total gas pressure is made up of the sum of the partial pressures of oxygen, carbon monoxide, olefin and hydrogen. The respective partial pressures may vary over a wide range based on the following considerations. Due to stoichiometric requirements, the olefin and hydrogen may generally be used in approximately equimolar amounts and hence their respective partial pressures are about equal. The oxygen partial pressure in the reaction system is somewhat limited due to safety considerations. As a result of this, it may not be possible to meet the stoichiometric requirements of the reaction for the generation of the carboxylic acid and its anhydride. In such an event, it may become necessary to periodically supply the reaction system with additional oxygen to thereby assure an adequate partial pressure of this component. Increasing the amount of oxygen does increase the selectivity of the reaction for an acid rather than an aldehyde product (i.e., below about 1 mole percent oxygen, there may be an insufficient selectivity for acid) although it at the same time appears to retard normal hydroformylation activity. Increasing the oxygen:hydrogen or oxygen::olefin ratio tends to improve selectivity toward carboxylated (i.e., acids and anhydrides) rather than non-carboxylated (i.e., aldehydes and ketones) products. Finally, variations in feed gas ratios do not seem to result in significant variations in the stability of the rhodium complex catalyst, except that catalyst stability is reduced under oxygen-containing when compared to oxygen-free hydroformylation reaction conditions.

Based on the foregoing, the hydroformylation-oxidation reaction may generally be conducted with a ratio of oxygen:carbon monoxide:olefin:hydrogen feed or make-up gas which is exposed to the reaction system (expressed as volume or mole percentages of the total gas feed-assuming compliance with the Ideal Gas Law) of about 1–5:30–70:5–35:5–35. The respective limits do not necessarily add up to 100% since each component may be adjusted relative to one or more of the other components to achieve a desired result, depending in part on the guidelines outlined above. A preferred gas ratio of $O_2$:CO:olefin:$H_2$ is about 2–3:50–60:20–30:20–30, and in the case of the most preferred reaction (ethylene to propionic acid), this gas ratio is about 3:50:23:23.

As noted above, the process is preferably conducted in an organic solvent inert to the conditions of reaction, preferably an inert aliphatic or aromatic organic solvent whose boiling point is at least as high as, but preferably greater than, the boiling point of the carboxylic acid being produced. Typical aliphatic inert solvents include saturated hydrocarbons having from about 9 to about 20 carbon atoms, such as nonane, undecane, dodecane and the like. These saturated hydrocarbons may be straight- or branched-chain, with the more highly-branched materials being preferred. Typical inert aromatic solvents include aromatic hydrocarbons such as benzene and biphenyl and aromatic hydrocarbons substituted by at least one saturated aliphatic hydrocarbon group, such as toluene, xylene, etc. Generally, the saturated aliphatic hydrocarbon substituent in these aromatic solvents may contain from 1 to about 15 carbon atoms and they may be straight-chain or branched-chain.

Generally, the particular solvent employed is not critical and the reaction conditions may be adjusted to prevent a solvent from becoming more volatile than the carboxylic acid produced. Optionally, the inert organic solvent may initially contain from 0.5 to 5 weight percent, based on the total weight of solvent, of the carboxylic acid being produced. The amount of acid in the solvent is not particularly critical since, in effect, this is a limit on how fast one desires to remove the acid produced from the reaction system. By providing acid in the reaction medium at the start of reaction, the formation of acid anhydride is favored over acid.

The amount of solvent that is employed in the practice of the present invention is limited only with respect to the catalyst; i.e. it must be at least that amount which will solubilize a catalytic quantity of rhodium. Generally, solvent is used to provide a rhodium concentration in the solvent of from about 25 parts per million (ppm) to about 1200 ppm, preferably from about 50 to about 400 ppm, of catalytically active rhodium calculated as the free metal. Regardless of the amount of or presence of solvent, the catalyst is employed in an amount to provide the indicated amount of catalytically-active rhodium.

The pentavalent Group V ligand may be represented by the formula:

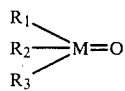

wherein M is a Group V metal such as phosphorus, arsenic or antimony; $R_1$, $R_2$ and $R_3$, which may be the same or different, each represents a straight- or branched-chain saturated hydrocarbon group (such as methyl, ethyl, propyl, isopropyl, n-butyl, sec-butyl, tert-amyl, hexyl, octyl, decyl, dodecyl), an aryl group (such as phenyl or biphenyl), a saturated straight- or branched-chain hydrocarbon-substituted aryl group (such as tolyl, xylyl, and the like) or an aryl-substituted straight- or branched-chain saturated hydrocarbon group (such as phenyl methyl, phenethyl). It is preferred that the number of carbon atoms in each of $R_1$, $R_2$ and $R_3$ does not exceed 15 and that the total number of carbon atoms in $R_1$, $R_2$ and $R_3$ does not exceed 30. The preferred ligands are those where M is phosphorus and $R_1$, $R_2$ and $R_3$ are the same straight-chain hydrocarbon group having from 5 to 8 carbon atoms. The most preferred ligand is tri(n-octyl) phosphine oxide.

The pentavalent Group V ligands may be obtained from commercial sources or may be made by conventional methods. For example, in the case of the preferred ligand, tri(n-octyl)phosphine oxide, tri(n-octyl) phosphine may be first prepared by methods known in the art and it may then be reacted with an oxidizing agent such as hydrogen peroxide or oxygen, followed by recovering the resulting phosphine oxide. See, for example, Harvie, et al., *Journal of the Chemical Society, Chemical Communications,* 369 (1976) and references cited therein.

The precise nature of the active rhodium complex catalyst species is unknown but is believed to consist essentially of rhodium stabilized by a pentavalent Group V ligand. The terminology "consist essentially of" is not meant to exclude, but rather to include, other ligands such as hydrogen and carbon monoxide if complexed with the rhodium under the conditions of the reaction. However, this language is meant to exclude other materials (such as halides and sulfur) in amounts which poison or deactivate the catalyst. What is known is that rhodium, in the presence of a pentavalent Group V ligand and the reactants employed in the hydroformylation-oxidation reaction, is a stable catalyst for producing a carboxylic acid from an olefin. It is theorized that the active rhodium complex catalyst species has no rhodium-bound halogen such as chlorine and the like species, and contains hydrogen, carbon monoxide and perhaps the pentavalent ligand complexed with rhodium metal to produce a catalyst which is normally soluble in liquids which may be used as a solvent in the reaction and which is stable under the conditions of reaction.

The active species, whatever its precise structure, may be obtained by two different techniques. An active rhodium complex catalyst precursor may be preformed and added to the hydroformylation-oxidation reaction mixture as such, or the necessary rhodium complex catalyst precursor ingredients may be introduced directly into the reaction mixture; in both cases, the active rhodium complex catalyst will be formed in situ. For example, an active rhodium complex catalyst precursor may be preformed as a solution by combining a rhodium compound, such as rhodium dicarbonyl acetylacetonate, and a suitable pentavalent ligand, such as tri(n-octyl)phosphine oxide. This precursor solution may then be added to the hydroformylation-oxidation reaction mixture to produce the active rhodium complex catalyst in situ. Alternatively, the necessary active rhodium catalyst precursor ingredients, i.e. a rhodium compound such as rhodium dicarbonyl acetylacetonate, or $Rh_4(CO)_{12}$ or $Rh_6(CO)_{16}$, and a pentavalent ligand such as tri(n-octyl)phosphine oxide, are added as such to the hydroformylation-oxidation reaction mixture. In any event, the active rhodium complex catalyst species is formed in situ in the reaction medium under the conditions existing therein. The latter technique, forming the active rhodium complex catalyst species by adding a rhodium compound and a ligand to the reaction medium is preferred. The pentavalent Group V ligand is added to the catalyst, regardless of how it is formed, in a sufficient amount to stabilize the catalyst against deactivation and generally to provide a concentration in the liquid reaction medium of from about 0.0008 to about 0.08 Molar, based on the volume of the total liquid reaction medium.

The hydroformylation-oxidation process of the invention is, as pointed out above, normally conducted in the liquid phase by feeding make-up gases into the liquid reaction medium. It is preferred to exclude from the liquid reaction medium, by conventional techniques, higher boiling liquid aldehyde condensation products which may be formed during the reaction inasmuch as they may not be inert to the reaction. For example, these and other by-products may be removed from time to time by distillation or extraction.

The process may be conducted in a continuous or in a batchwise or semi-batchwise fashion. In any event, it may be necessary to recharge the system with catalyst components from time to time. Whether such becomes necessary depends on several factors including the desired rate of reaction, the size of the reaction medium, the conditions of reaction, etc. Catalyst or components thereof may be added to the reaction medium by any suitable technique such as described above with regard to the initial catalyst charge.

The carboxylic acid produced may be recovered by any suitable and conventional technique, such as by distillation or extraction.

The second embodiment of the present invention involves the direct oxidation of an aldehyde to a carboxylic acid having the same number of carbon atoms as the aldehyde. This reaction (referred to herein for convenience as the aldehyde oxidation reaction) is also conducted in the presence of a rhodium complex catalyst which includes a pentavalent Group V ligand. The starting aldehyde can be obtained by any suitable technique, such as by hydroformylation of the corresponding olefin. According to the present invention, the aldehyde may have from 3 to about 21 carbon atoms although the preferred aldehyde is propionaldehyde which is treated in accordance with this embodiment to produce propionic acid.

The aldehyde oxidation reaction is generally conducted by feeding an oxygen-containing gas, such as air or diluted oxygen into a liquid reaction medium containing at least the starting aldehyde and a rhodium complex catalyst, for a sufficient period of time to oxidize the aldehyde to the corresponding acid. The reaction may be conducted at about atmospheric pressure but it is preferred to use a substantially constant pressure of about 1 to 2 atmospheres above atmospheric since, at these pressures, the catalyst is more stable as compared to stability at atmospheric pressure. It should be noted that at pressures substantially above atmospheric oxygen may become explosive and hence such pressures should be avoided. Generally, the maximum pressure of reaction is about 100 psig.

The aldehyde oxidation reaction is preferably conducted in an inert organic solvent, and in this case, the liquid reaction medium will initially comprise the aldehyde, the inert organic solvent and the rhodium complex catalyst. As reaction proceeds, the aldehyde content will of course decrease as acid is formed. The inert organic solvent may be the same as that described hereinabove with respect to the hydroformylation-oxidation reaction.

The aldehyde oxidation reaction may be conducted at a temperature of from about room temperature up to about 100° C. Beyond about 100° C., one needs to be concerned with the safety of the reaction since oxygen tends to become explosive with increasing temperature. In addition, there is no critical factor determining the minimum reaction temperature, although the rate of reaction generally decreases with decreasing temperature. The preferred reaction temperature is from about 40° to about 90° C. with higher temperatures generally providing higher rates of reaction.

The oxygen-containing gas fed to the liquid reaction medium generally contains from about 2 to 100% oxygen by volume. Typically, this gas stream comprises air or pure oxygen diluted with nitrogen and although it is possible and desirable to use a stoichiometric excess of oxygen with respect to the aldehyde, there is no advantage in employing too large an excess. Again, the maximum amount of oxygen in the gas stream fed to the liquid reaction medium would be determined primarily from a safety viewpoint considering the temperature and pressure of reaction.

It has been found, and it is therefore preferred, that the rhodium catalyst is more stable when carbon monoxide is also present in the reaction in an amount up to about equimolar based on air as an oxygen source.

The rhodium complex catalyst employed in this second embodiment may be obtained in the same manner and used in the same amounts as in the first embodiment of the invention described above; i.e., the same rhodium compounds and same stabilizing pentavalent Group V ligands as described above may be employed to obtain a stable rhodium complex catalyst.

Any conventional technique, such as those described above, can be employed to recover the carboxylic acid product and to remove undesired by-products from the reaction medium. In addition, the aldehyde oxidation reaction may also be conducted in a continuous or batchwise or semi-batchwise fashion as desired. Any conventional apparatus may be employed in both embodiments of the invention.

In both embodiments of this invention at least one of a carboxylic acid and its anhydride can be produced, i.e. either individually or as mixtures. Of course, the anhydride may be converted into its acid form by any conventional technique, such as by hydrolysis.

The invention will be further illustrated by reference to the following examples, some of which represent processes outside the scope of the invention for purposes of comparison.

EXAMPLE I

Into a 3-liter rocker bomb were charged a solvent, 0.12 g of rhodium dicarbonyl acetylacetonate, $Rh(CO)_2AcAc$, a ligand, and a mixture of 100 psi ethylene:100 psi carbon monoxide:100 psi hydrogen (total gas pressure: 300 psia), at an initial loading temperature of 30°–35° C. The system was then heated to 100±3° C. (unless otherwise indicated), the rocker was started and the system was maintained under those conditions for 4.5–5.5 hours by repressurizing with gas when necessary, cooled to 25° C., vented and the liquid contents isolated and analyzed by vapor phase chromatography (VPC) to determine the yield of propionaldehyde. The conditions and results are shown in Table I below. Although these runs are not within the scope of the present invention, they do illustrate that, under hydroformylation conditions, contrary to the trivalent Group VA ligands, their pentavalent analogues appear to function more effectively in the inert solvent toluene rather than acetophenone.

TABLE I

| | Ligand | | Reaction | Solvent | | Propionaldehyde |
|---|---|---|---|---|---|---|
| Run | Type | Amount (millimoles) | Temp. (°C.) | Type | Amount | Yield (g/hr) |
| 1 | Ph₃P | 20 | 80 | Acetophenone | 500g. | 22.7* |
| 2 | TOPO | 20 | 100 | " | " | 0.4 |
| 3 | Ph₃Sb | 20 | 100 | " | " | 4.4 |
| 4 | Ph₃SbO | 0.8 | 100 | " | " | 1.1 |
| 5 | Ph₃P | 36 | 80 | toluene | 500ml. | 14.3* |
| 6 | TOPO | 18 | 100 | " | " | 3.2* |
| 7 | TOPO | 18 | 100 | " | " | 2.9* |
| 8 | Ph₃Sb | 20 | 100 | " | " | 6.0 |
| 9 | Ph₃SbO | 0.8 | 100 | " | " | 1.5 |

Note:
*indicates runs in which a precipitate did not form in the final reaction solution and/or on reactor walls
Ph = phenyl
TOPO = tri(n-octyl) phosphine oxide

EXAMPLE II

The procedure of Example I was repeated except that the solvent (500 ml total) was varied and that di(rhodium dicarbonyl acetate), $(Rh(CO)_2OAc)_2$, was employed as a rhodium precursor instead of rhodium dicarbonyl acetylacetonate in run 26. The materials, conditions and results are shown in Table II below. None of these runs is within the scope of the present invention but the effect of the various solvents on a pentavalent phosphine oxide under hydroformylation conditions can be seen.

TABLE II

| | Ligand | | | Propionaldehyde |
|---|---|---|---|---|
| Run | Type | Amount (millimoles) | Solvent | Yield (g/hr) |
| 10 | None | | PhCOMe | 1.19 |
| 11 | TOPO | 18–20 | " | 0.40 |
| 12 | None | | PhCH₃ | 2.09 |
| 13 | TOPO | 4 | " | 0.90 |
| 14 | TOPO | 4 | " | 1.05 |
| 15 | TOPO | 18 | " | 2.90 |
| 16 | TOPO | 18 | " | 3.15 |
| 17 | None | | 75:25*PhCH₃:EtCO₂H | 6.60 |
| 18 | None | | 90:10 PhCH₃:EtCO₂H | 5.98 |
| 19 | None | | 97:3 PhCH₃:EtCO₂H | 5.55 |
| 20 | None | | 99:1 PhCH₃:EtCO₂H | 5.49 |
| 21 | TOPO | 4 | 97:3 PhCH₃:EtCO₂H | 4.67 |
| 22 | TOPO | 18 | 97:3 PhCH₃:EtCO₂H | 4.76 |
| 23 | TOPO | 18 | 97:3 PhCH₃:EtCO₂H | 4.89 |
| 24 | None | | 97:2.8 PhCH₃:AcOH | 4.63 |
| 25 | TOPO | 18 | 97:2.8 PhCH₃:AcOH | 4.38 |
| 26 | (Rh(CO)₂OAc)₂ | 0.5 | PhCH₃ | 4.30 |
| 27 | None | | 97:3 PhCH₃:PrOH (Ar) | 1.65 |
| 28 | None | | 97:3 PhCH₃:PrOH (Ar, purified) | 0.64 |
| 29 | TOPO | 18 | 97:3 PhCH₃:PrOH (Ar) | 1.20 |

*signifies parts by weight
Notes:
Ph = phenyl
TOPO = tri(n-octyl) phosphine oxide
Me and Et = methyl and ethyl respectively
AcOH = acetic acid
PrOH = propanol
Ar = analytical reagent grade

EXAMPLE III

The procedure of Example I was followed except that the ligands shown in Table III below were employed. At the completion of reaction, the amount of rhodium still retained in the liquid reaction medium was determined by atomic absorption and is shown in Table III as %Rh. The conditions and results are shown in Table III below. While none of these runs is within the scope of the invention, due to the absence of oxygen, the effect of the pentavalent ligand on rhodium stability is seen.

TABLE III

| | Ligand | | | |
|---|---|---|---|---|
| Run | Type | Amount (millimoles) | Solvent | % Rh** |
| 30 | Ph₃P | 36 | PhCH₃ | 100 |
| 31 | TOPO | 18 | PhCH₃ | 93 |
| 32 | TOPO | 18 | 97:3*PhCH₃:EtCO₂H | 96 |
| 33 | None | — | 97:3 PhCH₃:EtCO₂H | 79 |

*signifies parts by weight
**Data is relative to run No. 30 which had about 100% Rh retained in solution and recovered.
Notes:
Ph = phenyl
TOPO = tri(n-octyl) phosphine oxide
Et = ethyl

EXAMPLE IV

Into a 3-liter rocker bomb were charged, at a temperature of 30°–35° C., 0.12 g. of rhodium dicarbonyl acetylacetonate, $Rh(CO)_2AcAc$, a solvent mixture of toluene $(PhCH_3)$: propionic acid $(EtCO_2H)$ and ligand to provide an initial solution volume of 500 ml and a gas mixture having a total pressure of 300 psia, as shown in Table IV below. The system was then heated to 100±3° C. and the rocker was started. These temperature conditions were maintained for a period of 4.5 hours after which the rocker was cooled to 25°–30° C., vented and the liquid contents isolated and analyzed. The analysis was by VPC to determine the yield and distribution of products and by atomic absorption to determine the amount of rhodium which was retained in solution (shown as % Rh in Table IV). The conditions and results are shown in Table IV below. Except for Run no. 40, where 40 psi of a $CO:O_2$ mixture (96:4 by volume) was added at 3.8 hours, the pressure was allowed to decrease with reaction. Run nos. 34–36 are not within the scope of the invention and are included for comparison purposes only. Run nos. 37–41 illustrate the scope of the invention. Although no measurable acid was obtained in Run no. 37, the presence of TOPO does markedly improve rhodium stability compared to Run no. 36. The conditions of Run no. 37 include a relatively low $O_2$ partial pressure which in part accounts for the absence of acid product. (Compare Run nos. 42 and 44 in Example V which illustrate that acid can be obtained by suitably adjusting conditions other than $O_2$ partial pressure).

EXAMPLE V

The procedure of Example IV was repeated using 0.12 g. of rhodium dicarbonyl acetylacetonate, a reaction temperature of 100±3° C. and the conditions shown in Table V below. The amount of products was determined by VPC (within a margin of error of ±3% for aldehyde analysis and ±10–15% for acid or anhydride analysis) and the results are shown in Table V below. All of runs 42–45 illustrate the invention and how the conditions of reaction affect product distribution.

TABLE V

| | Ligand | | Solvent | | Gas Feed (psi) | | | | Product Amounts (g) | | |
|---|---|---|---|---|---|---|---|---|---|---|---|
| Run | Type | Amount (g) | Type | Amount | $O_2$ | CO | $C_2H_4$ | $H_2$ | EtCHO | $EtCO_2H$ | $(EtCO)_2O$ |
| 42 | TOPO | 4 | $PhCH_3$ | 500 ml | 4 | 96 | 100 | 100 | 10.6 | ≦0.5 | ≦1.0 |
| | | | $EtCO_2H$ | 2.5 g | | | | | | | |
| 43 | TOPO | 4 | $PhCH_3$ | 500 ml | 8 | 192 | 50 | 50 | 13.27 | 2.3 | 1.6 |
| | | | EtCHO | 4.0 g | | | | | | | |
| | | | $EtCO_2H$ | 2.5 g | | | | | | | |
| 44 | TOPO | 7 | $PhCH_3$ | 500 ml | 4 | 96 | 100 | 100 | 16.8 | ≦0.5 | 2.25 |
| | | | $EtCO_2H$ | 8.6 g | | | | | | | |
| 45 | TOPO | 7 | $PhCH_3$ | 500 ml | 8 | 192 | 50 | 50 | 9.23 | 1.7 | 1.8 |
| | | | $EtCO_2H$ | 2.5 g | | | | | | | |

NOTES:
In run no. 44, 40 psi of a $CO:O_2$ mixture (96:4 by volume) was added at 3.8 hours after start of the reaction.
TOPO = tri(n-octyl) phosphine oxide
$EtCO_2H$ = propionic acid
EtCHO = propionaldehyde
$(EtCO)_2O$ = propionic acid anhydride
$(Et)_2CO$ = diethyl ketone
Ph = phenyl

EXAMPLE VI

To a 0.1-liter Fisher-Porter bottle equipped with a magnetic stirrer was charged 70 cc. of toluene (blank run) or 70 cc. of a saturated solution of 8.29 g. of triphenylphosphine oxide (TPPO) in 90 g. of toluene, 5 cc. of a solution of 200 mg. of rhodium dicarbonyl acetylacetonate $(Rh(CO)_2AcAc)$ in 20 ml of toluene, 5 g. of propionaldehyde and 0.5 g. of acetic acid. The system was then heated to 50±3° C. using an oil bath and initially pressurized to 75 psia with a CO:Air mixture (1:1 by volume). This temperature and a pressure of 60–75 psia were maintained for 3.25 hours by repressurizing periodically with the same CO:air mixture, and thereafter the pressure was allowed to drop overnight. The system was then again repressurized to 70 psia and heated to a temperature of 52±3° C. This temperature was maintained for 4.5 hours while the pressure was allowed to decrease, after which the system was cooled to room temperature, vented and the liquid contents

TABLE IV

| | Ligand | | Solvent $PhCH_3:EtCO_2H$ | Gas Feed (psi) | | | | | Product Distribution (g) | | | |
|---|---|---|---|---|---|---|---|---|---|---|---|---|
| Run | Type | Amount (g) | (Weight ratio) | $O_2$ | CO | $C_2H_4$ | $H_2$ | % Rh | EtCHO | $EtCO_2H$ | $(EtCO)_2O$ | $(Et)_2CO$ |
| 34 | None | — | 97:3 | — | 100 | 100 | 100 | 79.0 | 25 | Nil | Nil | — |
| 35 | TOPO | 7 | 97:3 | — | 100 | 100 | 100 | 95.0 | 22 | Nil | Nil | — |
| 36 | None | — | 98:2 | 4 | 96 | 100 | 100 | 10.6 | 11.4 | Nil | Nil | 2.2 |
| 37 | TOPO | 7 | 98:2 | 4 | 96 | 100 | 100 | 82.0 | 15.8 | Nil | Nil | 1.7 |
| 38 | TOPO | 7 | 99:1 | 8 | 192 | 50 | 50 | 75.4 | 9.2 | 1.70 | 1.80 | 0.84 |
| 39 | TOPO | 4 | 99:1 | 8 | 192 | 50 | 50 | 68.0 | 10.0 | 2.00 | 1.75 | 0.96 |
| 40 | TOPO | 4 | 99:1 | 8 | 192 | 50 | 50 | 82.0 | 11.1 | 2.20 | 1.85 | 0.71 |
| | | | | (Addnl. CO and $O_2$ at T = 3.8 hr.) | | | | | | | | |
| 41 | TOPO | 4 | 99:1 | 10 | 240 | 25 | 25 | 84.0 | 1.5 | 1.65 | 1.90 | 0.15 |

NOTES:
TOPO = tri(n-octyl) phosphine oxide
$EtCO_2H$ = propionic acid
EtCHO = propionaldehyde
$(EtCO)_2O$ = propionic acid anhydride
$(Et)_2CO$ = diethyl ketone isolated and analyzed by VPC for the yield of propionic acid (EtCO$_2$H) and by atomic absorption to determine the amount of rhodium retained in solution. Comparable amounts of propionic acid, relative to the total products, were obtained in each run. The results are shown in Table VI below. Run no. 46 is outside the invention due to the absence of pentavalent ligand, while Run no. 47 illustrates the aldehyde oxidation embodiment of the invention.

TABLE VI

| Run | Ligand | % Rh |
|---|---|---|
| 46 | None | 47 |
| 47 | TPPO | 59 |

EXAMPLE VII

To the same 0.1-liter Fisher-Porter bottle as used in Example VI was charged 50 ml of toluene (PhCH$_3$) and 5 g. of tri(n-octyl) phosphine oxide (TOPO), or 5 g. of additional toluene (blank runs), along with 200 g. of rhodium carbonyl triphenylphosphine acetylacetonate, Rh(CO)(TPP)AcAc, 5 g. of propionaldehyde and 100 g. of acetic acid. The system was then charged with 30 psi of oxygen and heated to 40°±2° C. in an oil bath. The reaction solution was stirred and gas pressure maintained for 28 hours (followed in Run nos. 50 and 51 by 48 hours under the same gas pressure at 25° C.) by periodic addition of oxygen. Samples were taken at various times and analyzed by VPC for propionic acid, EtCO$_2$H, and propionic acid anhydride, (EtCO)$_2$O, and by atomic absorption for the amount (percentage) of rhodium still retained in solution. The conditions and results are shown in Table VII below. Run nos. 49 and 51 are outside the scope of the invention since no pentavalent ligand was present while Run nos. 48 and 50 illustrate the aldehyde oxidation embodiment of the invention.

TABLE VII

| Run | Ligand Type | Ligand Amount (g) | Solvent Type | Solvent Amount (ml) | Rhodium Recovery (%) | Products (g)* EtCO$_2$H | Products (g)* (EtCO)$_2$O |
|---|---|---|---|---|---|---|---|
| 48 | TOPO | 5 | PhCH$_3$ | 50 | 95 | 3 | — |
| 49 | None | — | PhCH$_3$ | 55 | 47 | 3 | — |
| 50 | TOPO | 5 | PhCH$_3$ | 50 | 82 | 4 | — |
| 51 | None | — | PhCH$_3$ | 55 | 62 | 4 | — |

*These are the averages of several samples.

It should be understood that the foregoing description is merely illustrative of the present invention and that various modifications and variations of this invention will be obvious to a worker skilled in the art and it is to be understood that such modifications and variations are to be included within the purview of this application and the spirit and scope of the appended claims.

What is claimed is:

1. A process for preparing at least one of a carboxylic acid and its anhydride directly from an olefin comprising reacting the olefin with carbon monoxide, hydrogen and oxygen in the presence of a rhodium complex catalyst consisting essentially of rhodium stabilized by a pentavalent Group V ligand represented by the formula

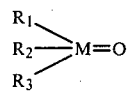

wherein R$_1$, R$_2$ and R$_3$, which may be the same or different, each represents a member selected from the group consisting of an alkyl group, an aryl group, an alkyl-substituted aryl group and an aryl-substituted alkyl group; and wherein M represents a Group V element selected from the group consisting of phosphorus, arsenic and antimony.

2. A process according to claim 1, wherein said olefin is a mono-olefin having from two to about twenty carbon atoms.

3. A process according to claim 2 wherein said mono-olefin is an alpha-olefin.

4. A process according to claim 2, wherein said mono-olefin is an internal olefin.

5. A process according to claim 1, wherein each of said R$_1$, R$_2$ and R$_3$ contains no more than 15 carbon atoms and wherein the total number of carbon atoms in said R$_1$, R$_2$ and R$_3$ is no more than 30 carbon atoms.

6. A process according to claim 5, wherein each of said R$_1$, R$_2$ and R$_3$ comprises a saturated straight-chain hydrocarbon group having from 5 to 8 carbon atoms.

7. A process according to claim 6, wherein M represents phosphorus.

8. A process according to claim 1, wherein said ligand is trioctylphosphine oxide.

9. A process according to claim 1, wherein the temperature and total pressure of said reaction are about 95° to about 110° C. and from about 250 to about 350 lbs. per square inch absolute, respectively.

10. A process according to claim 1, wherein said reaction is conducted in an inert organic solvent.

11. A process according to claim 10, wherein said inert organic solvent is an aliphatic or aromatic hydrocarbon.

12. A process according to claim 10, wherein said inert organic solvent is a member selected from the group consisting of a saturated aliphatic hydrocarbon having from about 9 to about 20 carbon atoms, benzene and an aromatic hydrocarbon substituted by at least one saturated aliphatic hydrocarbon group having from 1 to about 15 carbon atoms.

13. A process according to claim 10, wherein said reaction is conducted by exposing a liquid reaction mixture comprising said solvent and said rhodium complex catalyst to a gas stream comprising oxygen, carbon monoxide, olefin and hydrogen.

14. A process according to claim 13, wherein the molar ratio oxygen:carbon monoxide:olefin:hydrogen in said gas stream is about 1-5:30-70:5-35:5-35.

15. A process according to claim 13, wherein the concentration of catalytically active rhodium in said solvent is from about 25 to about 1200 parts per million, calculated as the free metal.

16. A process according to claim 13, wherein the concentration of said ligand in said liquid reaction medium is from about 0.0008 to about 0.08 Molar, based on the total volume of liquid reaction medium.

17. A process according to claim 13, wherein said solvent also contains from about 0.5 to about 5 weight percent, based on the weight of the total liquid reaction medium, of said carboxylic acid.

18. A single-step process for preparing at least one of a carboxylic acid and its anhydride having from 3 to 21 carbon atoms directly from a mono-olefin having correspondingly from 2 to 20 carbon atoms comprising reacting said olefin with carbon monoxide, hydrogen and oxygen in an inert organic solvent and in the presence of a rhodium complex catalyst consisting essentially of rhodium stabilized by a pentavalent phosphorus ligand represented by the formula

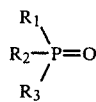

wherein $R_1$, $R_2$ and $R_3$ each represents a saturated straight-chain hydrocarbon group having from 5 to 8 carbon atoms.

19. A process according to claim 18, wherein said olefin is ethylene.

20. A process according to claim 18, wherein said inert organic solvent is a member selected from the group consisting of a saturated aliphatic hydrocarbon having from about 9 to about 20 carbon atoms, benzene and an aromatic hydrocarbon substituted with at least one saturated aliphatic hydrocarbon group having from 1 to about 15 carbon atoms.

21. A process according to claim 19, wherein said inert organic solvent is toluene.

22. A process according to claim 21, wherein said pentavalent phosphorus ligand is trioctylphosphine oxide.

23. A process according to claim 22, wherein said liquid reaction medium also initially includes from about 0.5 to about 5 weight percent, based on the total weight of the liquid reaction medium, of said carboxylic acid.

24. A process according to claim 23, wherein the molar ratio oxygen:carbon monoxide:ethylene:hydrogen is about 2–3:50–60:20–30:20–30.

* * * * *